US010214467B2

(12) United States Patent
Vonner et al.

(10) Patent No.: US 10,214,467 B2
(45) Date of Patent: Feb. 26, 2019

(54) SIMULATED MOVING BED XYLENES SEPARATION PROCESS, AND OPTIMIZED OPERATING CONDITIONS FOR UNITS TREATING PARAXYLENE-RICH FEEDS

(71) Applicant: IFP Energies nouvelles, Rueil-Malmaison (FR)

(72) Inventors: Alexandre Vonner, Feyzin (FR); Damien Leinekugel Le Cocq, Oullins (FR); Catherine Laroche, Vernaison (FR); Pascal Etienne, Estrablin (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 15/982,649

(22) Filed: May 17, 2018

(65) Prior Publication Data
US 2018/0334415 A1   Nov. 22, 2018

(30) Foreign Application Priority Data
May 17, 2017  (FR) ...................... 17 54360

(51) Int. Cl.
*C07C 7/13* (2006.01)
*B01D 15/18* (2006.01)

(52) U.S. Cl.
CPC .............. *C07C 7/13* (2013.01); *B01D 15/185* (2013.01); *B01D 15/1828* (2013.01)

(58) Field of Classification Search
None
See application file for complete search history.

(56) References Cited

U.S. PATENT DOCUMENTS

| | | | | |
|---|---|---|---|---|
| 4,434,051 A * | 2/1984 | Golem | ............... | B01D 15/1842 210/264 |
| 5,223,143 A * | 6/1993 | Masuda | ............. | B01D 15/1828 127/46.1 |
| 5,470,482 A | 11/1995 | Holt | | |
| 2002/0055665 A1 * | 5/2002 | Pavone | ................... | C07C 7/005 585/825 |
| 2004/0118781 A1 * | 6/2004 | Ma | ..................... | B01D 15/1828 210/656 |
| 2009/0218380 A1 | 9/2009 | Prittie | | |
| 2009/0326309 A1 | 12/2009 | Priegnitz et al. | | |
| 2011/0201865 A1 * | 8/2011 | Decoodt | ........... | B01D 15/1835 585/822 |
| 2011/0315634 A1 * | 12/2011 | Hotier | ............... | B01D 15/1835 210/659 |
| 2013/0153500 A1 * | 6/2013 | Frey | ......................... | C07C 7/13 210/660 |
| 2013/0158335 A1 * | 6/2013 | Corradi | ..................... | C07C 7/12 585/828 |
| 2014/0121436 A1 * | 5/2014 | Leflaive | ............ | B01D 15/1828 585/805 |
| 2015/0087876 A1 * | 3/2015 | Sanger | ...................... | C07C 7/12 585/805 |
| 2016/0046545 A1 * | 2/2016 | Maher | ..................... | C07C 7/005 585/805 |
| 2016/0145174 A1 * | 5/2016 | Porter | ................. | B01D 15/1807 585/828 |
| 2017/0130163 A1 * | 5/2017 | Kelliher | ............... | B01D 15/185 |
| 2017/0305818 A1 * | 10/2017 | Porter | ............... | B01D 15/1835 |
| 2018/0009729 A1 * | 1/2018 | Ou | ......................... | C07C 15/073 |
| 2018/0161696 A1 * | 6/2018 | Oroskar | ............... | B01D 15/185 |

FOREIGN PATENT DOCUMENTS

WO   2009019336 A1   2/2009

OTHER PUBLICATIONS

French Application No. 1754360 search report dated Jan. 18, 2018 (p. 1-7).

* cited by examiner

*Primary Examiner* — Tam M Nguyen
(74) *Attorney, Agent, or Firm* — Millen, White, Zelano and Branigan, P.C.

(57) ABSTRACT

The present invention describes a process for the simulated moving bed separation of xylenes which can be used for the treatment of paraxylene-rich feeds (more than 25% by weight of paraxylene), in which the operating conditions are optimized by means of a specific relationship between the cycle time and the desorbant flow rate.

4 Claims, No Drawings

SIMULATED MOVING BED XYLENES SEPARATION PROCESS, AND OPTIMIZED OPERATING CONDITIONS FOR UNITS TREATING PARAXYLENE-RICH FEEDS

CONTEXT OF THE INVENTION

The present invention relates to the field of the separation of paraxylene from other C8 aromatic isomers. In order to carry out this separation, a family of processes and associated devices are used which are known by the term "simulated moving bed separation processes" (abbreviated to SMB), or "simulated counter-current separation" (abbreviated to SCC), or in fact the "VARICOL process", which we shall hereinafter designate by the general title of SCC separation processes. More precisely, the aim of the present invention is to optimize the operating conditions for a given unit by obtaining a cycle time as a function of the flow rate of the desorbant with respect to the flow rate of paraxylene contained in the feed, in the case of unconventional paraxylene-rich feeds. The term "paraxylene-rich feeds" means feeds with a paraxylene content of more than 25% by weight, and more particularly in the range 25.01% to 60% by weight.

EXAMINATION OF THE PRIOR ART

SCC separation is well known in the prior art. As a general rule, a paraxylene separation process operating in simulated counter-current mode comprises at least four zones, and possibly five or six, each of these zones being constituted by a certain number of successive beds, and each zone being defined by its position between a supply point and a withdrawal point. Typically, a SCC unit for the production of paraxylene is supplied with at least one feed F to be fractionated (containing paraxylene and the other C8 aromatic isomers) and a desorbant D, sometimes known as the eluent (generally paradiethylbenzene or toluene), and at least one raffinate R containing the isomers of paraxylene and desorbant and an extract E containing paraxylene and desorbant are withdrawn from said unit.

Simulated moving bed processes for the separation of xylenes are conventionally operated with adjustments which are intended to maximize productivity, at the cost of a high flow of desorbant, and thus a high utilities cost (reboiling of distillation columns, pumps, etc).

The present invention concerns the field of low desorbant ratios, i.e. the field of low ratios between the flow rate of desorbant and the flow rate of feed, where a compromise is reached between productivity and reducing the desorbant flow rate, and therefore reducing the operating costs.

We have not found any prior art which specifically pertains to the link between the flow rate of desorbant and the cycle time, i.e. the time over which the injections and withdrawals from the unit shift along the column until they return to their initial position. Moreover, we have not found any disclosures of this type for feeds with high paraxylene contents with which the present invention is concerned.

BRIEF DESCRIPTION OF THE INVENTION

The present invention describes a series of optimized adjustments for a simulated moving bed unit for the separation and purification of paraxylene contained in a feed of C8 isomers, the paraxylene content in the feed being in the range 25.01% to 60% by weight, and the ethylbenzene content being in the range 2% to 15% by weight. The term "optimized adjustment" should be understood to mean that the purity and yield performances as well as the maximum paraxylene productivity are reached for a given desorbant flow rate. The simulated moving bed xylenes separation unit uses at least one column for which the number of beds is in the range 4 to 24, preferably in the range 6 to 18, and more preferably in the range 8 to 15.

The configuration of the unit may be defined by defining the mean number of beds for the zone j (j being in the range 1 to 4), Nzj, with respect to the total number of beds in the unit as a whole, N_total, as follows:

$$Nz1 = (N\_total * 5/24) * (1 \pm 0.2)$$

$$Nz2 = (N\_total * 9/24) * (1 \pm 0.2)$$

$$Nz3 = (N\_total * 7/24) * (1 \pm 0.2)$$

$$Nz4 = (N\_total * 3/24) * (1 \pm 0.2)$$

The 4 chromatographic zones are defined as follows:
Zone 1: paraxylene desorption zone, included between the injection of the desorbant D and the withdrawal of the extract E;
Zone 2: zone for the desorption of isomers of paraxylene, included between the withdrawal of the extract E and the injection of the feed to be fractionated F;
Zone 3: paraxylene adsorption zone, included between the injection of the feed and the withdrawal of the raffinate R;
Zone 4: zone located between the withdrawal of the raffinate R and the injection of the desorbant D.

The desorbant used in the context of the present invention is paradiethylbenzene.

The optimized adjustments for the simulated moving bed are described in the form of desorbant ratio pairs for a weighted cycle time.

The desorbant ratio is the ratio of the flow rate of desorbant to the flow rate of paraxylene contained in the feed.

The cycle time is the time interval between two injections of desorbant to the same location in the adsorber. It is known here as the "weighted" time when it is multiplied by the factor $$\frac{\mu}{\sigma^2} \cdot \frac{1}{\varepsilon_i \cdot L_{lit}}$$

The ratio $$\frac{\mu}{\sigma^2},$$

expresses in units of 1/s, is determined by a breakthrough experiment, as will be described in more detail below in the detailed description of the invention.

It is important to ensure that the measurement $\sigma^2$ is representative of the overall material transfer in the adsorbent, and not of the dispersion linked to the hydrodynamics in the column and in the lines of the test tool. To this end, a breakthrough test must be carried out under the same conditions as the test carried out with a column filled with adsorbent, but filling the column with glass beads with a diameter comparable to the diameter of the adsorbent. The measurement of $\sigma^2$ obtained in the presence of adsorbent must be at least 10 times higher, preferably 30 times higher than the measurement $\sigma^2_{blank}$ obtained during this test in the absence of adsorbent.

$L_{lit}$ represents the length of a bed, expressed in metres, and $\varepsilon_i$ represents the mean interstitial porosity of a bed of adsorbent.

The optimized cycle time (interval of time between two injections of desorbant to the same location in the column) is determined from the weighted cycle time using the factor:

$$\frac{\mu}{\sigma^2} \cdot \frac{1}{\varepsilon_i \cdot L_{lit}}$$

Knowing the length of a bed ($L_{lit}$) and its interstitial porosity ($\varepsilon_i$), the ratio of the flow rate of desorbant to the flow rate of paraxylene and thus the desired optimal desorbant flow rate ($Q_D$) is determined over the range of paraxylene concentration (PX) in the feed by means of the following three tables, $Q_{PX}$ designating the entering paraxylene flow rate:

TABLE 1

Paraxylene PX in the feed: 25% < %$_{PX\_feed}$ ≤ 30%

| | t_cycle wtd (1/m) | $Q_D/Q_{PX}$ |
|---|---|---|
| Adjustment No 1 | 320 +/− 25 | 5.30 +/− 0.55 |
| Adjustment No 2 | 345 +/− 25 | 4.85 +/− 0.50 |
| Adjustment No 3 | 370 +/− 25 | 4.50 +/− 0.45 |
| Adjustment No 4 | 395 +/− 25 | 4.20 +/− 0.45 |
| Adjustment No 5 | 425 +/− 25 | 4.00 +/− 0.45 |
| Adjustment No 6 | 465 +/− 25 | 3.75 +/− 0.40 |
| Adjustment No 7 | 510 +/− 25 | 3.60 +/− 0.40 |
| Adjustment No 8 | 560 +/− 30 | 3.55 +/− 0.40 |

TABLE 2

Paraxylene PX in the feed: 30% < %$_{PX\_feed}$ ≤ 45%

| | t_cycle wtd (1/m) | $Q_D/Q_{PX}$ |
|---|---|---|
| Adjustment No 1 | 325 +/− 25 | 4.40 +/− 0.45 |
| Adjustment No 2 | 345 +/− 25 | 4.00 +/− 0.40 |
| Adjustment No 3 | 365 +/− 25 | 3.75 +/− 0.40 |
| Adjustment No 4 | 385 +/− 25 | 3.50 +/− 0.40 |
| Adjustment No 5 | 415 +/− 25 | 3.30 +/− 0.35 |
| Adjustment No 6 | 445 +/− 25 | 3.15 +/− 0.35 |
| Adjustment No 7 | 485 +/− 25 | 3.00 +/− 0.35 |
| Adjustment No 8 | 530 +/− 25 | 2.90 +/− 0.35 |
| Adjustment No 9 | 580 +/− 30 | 2.80 +/− 0.30 |
| Adjustment No 10 | 640 +/− 30 | 2.80 +/− 0.30 |

TABLE 3

Paraxylene PX in the feed: 45% < %$_{PX\_feed}$ ≤ 60%

| | t_cycle wtd (1/m) | $Q_D/Q_{PX}$ |
|---|---|---|
| Adjustment No 1 | 315 +/− 25 | 4.10 +/− 0.50 |
| Adjustment No 2 | 335 +/− 25 | 3.65 +/− 0.45 |
| Adjustment No 3 | 350 +/− 25 | 3.25 +/− 0.35 |
| Adjustment No 4 | 370 +/− 25 | 3.05 +/− 0.35 |
| Adjustment No 5 | 400 +/− 25 | 2.80 +/− 0.35 |
| Adjustment No 6 | 440 +/− 25 | 2.65 +/− 0.30 |
| Adjustment No 7 | 480 +/− 25 | 2.55 +/− 0.30 |
| Adjustment No 8 | 525 +/− 25 | 2.45 +/− 0.30 |
| Adjustment No 9 | 580 +/− 30 | 2.40 +/− 0.30 |
| Adjustment No 10 | 640 +/− 30 | 2.35 +/− 0.30 |

The operating conditions for the simulated moving bed xylenes separation process in accordance with the invention are as follows:

the operating temperature is generally in the range 100° C. to 250° C., preferably in the range 120° C. to 180° C., and the pressure is in the range between the bubble pressure of the mixture of xylenes constituting the feed and 3 MPa.

The water content in the feed for the simulated moving bed xylenes separation process in accordance with the invention is generally in the range 70 to 140 ppm, and preferably in the range 80 to 120 ppm.

The desorbant used in the xylenes separation process in accordance with the present invention is paradiethylbenzene.

DETAILED DESCRIPTION OF THE INVENTION

The problem which the present invention seeks to resolve is that of an optimized adjustment of the process with a low desorbant ratio range, in order to reduce the "run-around" and optimize the operating expenses (OPEX) of the process. The term "optimized adjustment" should be understood to mean an adjustment which may be used to obtain a minimum flow rate of desorbant for a given level of productivity, while at the same time guaranteeing the required levels of purity and yield: typically, a paraxylene purity of more than 99.5%, preferably more than 99.6%, and more preferably more than 99.7%, and a paraxylene yield of more than 95%, preferably more than 96%, and more preferably more than 97%. In the current state of the art, there are no methods for the optimized adjustment of a xylenes separation unit.

The invention concerns a process for the production of high purity paraxylene starting from a feed F which is termed unconventional, which is rich in paraxylene, i.e. comprising between 25.01% and 60% by weight of paraxylene, associated with its other C8 aromatic isomers.

In accordance with one characteristic of the process, the adsorbent for the process in accordance with the invention is a zeolitic adsorbent based on crystals of X zeolite and a non-zeolitic phase, preferably a zeolite of the faujasite type exchanged with barium or exchanged with barium and potassium.

Separation of commercial purity paraxylene using SMB, typically to at least 99.7% by weight, is carried out industrially in SMB equipment comprising n beds of adsorbents, n possibly being in the range 4 to 24, preferably in the range 6 to 18 beds, and more preferably in the range 8 to 15 beds. The number of beds is adjusted in a manner such that each bed preferably has a height in the range 70 cm to 1.40 m.

The configuration of each zone, i.e. the mean number of beds per zone of the unit in accordance with the invention, may have a number of beds which is fixed (the shifts for the various injection or withdrawal points thus being simultaneous) or variable. In this latter case, the shifts for the 2 injection points and the 2 withdrawal points are not simultaneous, so as to obtain mean numbers of beds per zone which are not whole numbers during a cycle, as taught in the patent FR2785196.

The configuration of the unit may be defined by defining the mean number of beds for the zone j (j being in the range 1 to 4), Nzj, with respect to the total number of beds in the unit as a whole, N_total, as follows. In these expressions, the first index z is the number of beds in the zone under consideration, and the second index j, which varies from 1 to 4, represents the zone under consideration.

$$Nz1=(N\_total*5/24)*(1\pm0.2)$$

$$Nz2=(N\_total*9/24)*(1\pm0.2)$$

$$Nz3=(N\_total*7/24)*(1\pm0.2)$$

$$Nz4=(N\_total*3/24)*(1\pm0.2)$$

By applying the above formulae, it is possible for the numbers of beds to turn out to be non-integral. This does not cause a problem in the context of the present invention, because there is a variation of the Eluxyl process known as the "Varicol" variation which allows such an operation.

The 4 chromatographic zones are generally defined as follows:
Zone 1: paraxylene desorption zone, included between the injection of the desorbant D and the withdrawal of the extract E;
Zone 2: zone for the desorption of isomers of paraxylene, included between the withdrawal of the extract E and the injection of the feed to be fractionated F;
Zone 3: paraxylene adsorption zone, included between the injection of the feed and the withdrawal of the raffinate R;
Zone 4: zone located between the withdrawal of the raffinate R and the injection of the desorbant D.

Advantageously, the cycle time, corresponding to the time between two injections of desorbant into a given bed, is in the range 3 to 50 min, preferably in the range 5 to 45 min.

Advantageously, the xylenes separation process is operated at a temperature of 175° C.±10° C., and at a pressure in the range from the bubble pressure of xylenes at the temperature of the process to 3 MPa.

Advantageously, the recycle ratio is in the range 2.0 to 8, preferably in the range 2.5 to 5. The recycle ratio is defined as the ratio between the mean flow rate flowing in the various beds of the adsorber to the flow rate of injecting feed into that adsorber.

The water content in the liquid phase is kept to a level in the range 80 to 120 ppm (by weight).

In the paraxylene separation process in accordance with the invention, the desorbant is paradiethylbenzene.

In addition to a high adsorption capacity and good selectivity properties as regards the species to be separated from the reaction mixture, the adsorbent must have good material transfer properties in order to guarantee a sufficient number of theoretical plates to carry out efficient separation of the species which are in the mixture, as indicated by Ruthven in the publication entitled "Principles of Adsorption and Adsorption Processes", John Wiley & Sons, (1984), pages 326 and 407.

In order to estimate the overall material transfer of a bed of adsorbent, a simple technique consists of carrying out a chromatographic experiment in which the adsorbent packed into a column undergoes a perturbation to the concentration at the column inlet. This technique has been described in the following document:

Silva, M. S. P.; Moreira, M. A.; Ferreira, A. F. P.; Santos, J. C.; Silva, V. M. T. M.; Sá Gomes, P.; Minceva, M.; Mota, J. P. B.; Rodrigues, A. E. Adsorbent Evaluation Based on Experimental Breakthrough Curves: Separation of p-Xylene from C8 Isomers. Chem. Eng. Technol. 2012, 35, 1777-1785.

The analysis of the concentration front at the outlet from the column as a function of time, denoted c(t), in response to the perturbation of the concentration at the inlet can be used to estimate the adsorption properties and the overall material transfer.

When the perturbation at the inlet is a function of concentration, the experiment which is carried out is known by the name of "breakthrough" and the concentration front obtained at the outlet from the column as a function of time is known as the "breakthrough curve".

In the publication entitled "Diffusion in Nanopores", by Kärger, Ruthven and Theodorou, Wiley (2012), the analysis of the experimental response of a chromatographic column by the method of moments is described in Chapter 14, pages 464-465.

In the case of a breakthrough as a response to a function of concentration $c_0$, the first and second moments of the concentration front c(t) at the outlet from the column as a function of time are given by the following expressions:

$\mu$, the first moment of the breakthrough curve, i.e. the mean outlet time $\bar{t}$ of the concentration front from the chromatographic column:

$$\mu = \bar{t} = \int_0^\infty \left(1 - \frac{c}{c_0}\right) dt$$

$\sigma^2$, the second moment centred on the breakthrough curve, which translates as the dispersion of the concentration front:

$$\sigma^2 = 2\int_0^\infty \left(1 - \frac{c}{c_0}\right) t\, dt - \mu^2$$

c(t) is the concentration function as a function of time following a perturbation $c_0$ introduced into the inlet.

It is important to ensure that the measurement of $\sigma^2$ is representative of the overall material transfer in the adsorbent and not of the dispersion linked to the hydrodynamics in the column and in the lines of the test equipment. For this reason, a breakthrough test must be carried out under the same conditions as the test carried out with a column filled with adsorbent, but filling the column with glass beads with a diameter approximately equal to the diameter of the particles of adsorbent. The measurement of $\sigma^2$ obtained in the presence of adsorbent must be at least 10 times higher, preferably 30 times higher than the measurement $\sigma^2_{blank}$ obtained during this test in the absence of adsorbent. The term "approximately equal" means the same as plus or minus 10%.

The cycle time is one of the operating parameters, like the flow rates for the injection of feed, of desorbant, and the flow rates for withdrawal of extract and raffinate, which are defined on a case by case basis by the operators of the process. There is no systematic adjustment method which exists in the current state of the art.

The present invention describes the relationship between:
the desorbant ratio, expressed as the ratio of the flow rate of desorbant, $Q_D$, over the flow rate of paraxylene in the feed, $Q_{PX}$;
$t_{cycle}$, the minimal cycle time of the process, weighted by the ratio of the first breakthrough moment $\mu$ over the product of the second centred moment of the break through $\sigma^2$; $L_{lit}$, the length of a bed, and $\varepsilon_i$, the porosity of the stack of solid adsorbent:

$$t_{cycle,weighted} = t_{cycle} \cdot \frac{\mu}{\sigma^2} \cdot \frac{1}{\varepsilon_i L_{lit}}$$

The weighted cycle time is thus linked to the cycle time by a group of parameters which are the first and second moments of the breakthrough curve obtained experimentally, and two parameters of the bed: its length ($L_{lit}$) and its interstitial porosity ($\varepsilon_r$). This weighted cycle time thus has the dimension of a reciprocal length and is therefore expressed as 1/m.

The described invention is valid irrespective of the material transfer properties of the adsorbent solid and the configuration of the process, which are included in the weighting factor for the cycle time.

The first and second breakthrough moments are determined for a given superficial velocity of the mixture injected during the breakthrough experiment, equal to 1.30 cm/s±0.05 cm/s under the temperature conditions of the test, i.e. 175° C., and for a given length of the column of 1.00 m±0.01 m.

The optimized adjustments described by the invention are presented in the 3 tables below, which cover the range for the paraxylene concentration in the feed:

TABLE 1

| 25% < Paraxylene PX in the feed ≤ 30% | | |
| 25% < Paraxylene PX in the feed ≤ 30% | | |
| --- | --- | --- |
| | t_cycle wtd (1/m) | $Q_D/Q_{PX}$ |
| Adjustment No 1 | 320 +/− 25 | 5.30 +/− 0.55 |
| Adjustment No 2 | 345 +/− 25 | 4.85 +/− 0.50 |
| Adjustment No 3 | 370 +/− 25 | 4.50 +/− 0.45 |
| Adjustment No 4 | 395 +/− 25 | 4.20 +/− 0.45 |
| Adjustment No 5 | 425 +/− 25 | 4.00 +/− 0.45 |
| Adjustment No 6 | 465 +/− 25 | 3.75 +/− 0.40 |
| Adjustment No 7 | 510 +/− 25 | 3.60 +/− 0.40 |
| Adjustment No 8 | 560 +/− 30 | 3.55 +/− 0.40 |

TABLE 2

| 30% < Paraxylene PX in the feed ≤ 45% | | |
| 30% < Paraxylene PX in the feed ≤ 45% | | |
| --- | --- | --- |
| | t_cycle wtd (1/m) | $Q_D/Q_{PX}$ |
| Adjustment No 1 | 325 +/− 25 | 4.40 +/− 0.45 |
| Adjustment No 2 | 345 +/− 25 | 4.00 +/− 0.40 |
| Adjustment No 3 | 365 +/− 25 | 3.75 +/− 0.40 |
| Adjustment No 4 | 385 +/− 25 | 3.50 +/− 0.40 |
| Adjustment No 5 | 415 +/− 25 | 3.30 +/− 0.35 |
| Adjustment No 6 | 445 +/− 25 | 3.15 +/− 0.35 |
| Adjustment No 7 | 485 +/− 25 | 3.00 +/− 0.35 |
| Adjustment No 8 | 530 +/− 25 | 2.90 +/− 0.35 |
| Adjustment No 9 | 580 +/− 30 | 2.80 +/− 0.30 |
| Adjustment No 10 | 640 +/− 30 | 2.80 +/− 0.30 |

TABLE 3

| 45% < Paraxylene PX in the feed ≤ 60% | | |
| 45% < Paraxylene PX in the feed ≤ 60% | | |
| --- | --- | --- |
| | t_cycle wtd (1/m) | $Q_D/Q_{PX}$ |
| Adjustment No 1 | 315 +/− 25 | 4.10 +/− 0.50 |
| Adjustment No 2 | 335 +/− 25 | 3.65 +/− 0.45 |
| Adjustment No 3 | 350 +/− 25 | 3.25 +/− 0.35 |

TABLE 3-continued

| 45% < Paraxylene PX in the feed ≤ 60% | | |
| 45% < Paraxylene PX in the feed ≤ 60% | | |
| --- | --- | --- |
| | t_cycle wtd (1/m) | $Q_D/Q_{PX}$ |
| Adjustment No 4 | 370 +/− 25 | 3.05 +/− 0.35 |
| Adjustment No 5 | 400 +/− 25 | 2.80 +/− 0.35 |
| Adjustment No 6 | 440 +/− 25 | 2.65 +/− 0.30 |
| Adjustment No 7 | 480 +/− 25 | 2.55 +/− 0.30 |
| Adjustment No 8 | 525 +/− 25 | 2.45 +/− 0.30 |
| Adjustment No 9 | 580 +/− 30 | 2.40 +/− 0.30 |
| Adjustment No 10 | 640 +/− 30 | 2.35 +/− 0.30 |

The points defined in the above 3 tables describe the optimized adjustments in the sense that the productivity of paraxylene is a maximum for the desorbant ratio under consideration.

The adjustments with a low desorbant ratio or with a smaller weighted cycle time cannot be used to obtain the purity targets and yield of the process.

The adjustments at a higher desorbant ratio or a higher weighted cycle time can be used to obtain performances, but either the paraxylene productivity is lower than its optimized value, or the desorbant ratio is not as low as possible for that productivity. Thus, they are made as close as possible to these optimized adjustments which are the objective of the invention.

Examples in Accordance with the Invention

The invention will be better understood from the three examples below. The first corresponds to a unit which is adjusted in an optimized manner in accordance with the invention, the second to an "under-performing" unit adjusted to the same desorbant ratio, and the third to an "over-performing" unit adjusted to the same desorbant ratio.

A breakthrough test (chromatographic front) was carried out on the adsorbents with the aim of evaluating the reduced second moment $$\frac{\sigma^2}{2\mu^2}$$

as a function of the superficial velocity of the injected fluid. The breakthrough consists of continuously injecting a feed containing one or more compounds which will be adsorbed through a column filled with adsorbent. The column was pre-saturated with solvent. The column used had a length of 1.00 metre and an internal diameter of 0.77 cm, and the quantity of adsorbent solid for this test was approximately 40 g.

The mode of operation in order to obtain the breakthrough curves was as follows:

Filling the column with adsorbent solid and placing on a test bench.

Filling with solvent at ambient temperature.

Gradually raising the adsorption temperature in a stream of solvent (flow rate at ambient temperature set to 5 cm³/min).

Injection of solvent at 30 cm³/min (set flow rate at ambient temperature) when the adsorption temperature is reached.

Solvent/feed permutation to inject the feed (flow rate at ambient temperature set to 30 cm³/min).

Continuous collection of breakthrough effluent in sealed vials as required, and measurement and analysis of the effluent collected in the vials by gas phase chromatography.

Maintaining the injection of the feed for a time sufficient to obtain thermodynamic equilibrium (i.e. until the concentration of solvent in the effluent is zero).

In order to obtain the breakthrough curve, the solvent used was orthoxylene. The feed used consisted solely of metaxylene.

The test was carried out at an adsorption temperature of 175° C. The pressure was sufficient for the feed to remain in the liquid phase, i.e. 1 MPa.

Two tests were carried out: a test with the column filled with glass beads with a granulometry of 400-600 μm from which $\sigma^2_{blank}$ was evaluated, and a second test with the same column (or an identical column) filled with adsorbent with a granulometry of 400-600 μm, from which the first moment μ and the second centred moment $\sigma^2$ were calculated.

The results are summarized in Table 4 below:

TABLE 4

| Determination of second moment from a breakthrough experiment | | |
|---|---|---|
| Superficial velocity of liquid | 1.30 | cm/s |
| $\sigma^2_{blank}$ | 0.001 | min$^2$ |
| $1^{st}$ moment μ | 0.98 | min |
| $\sigma^2$ | 0.129 | min$^2$ |
| $\sigma^2/\sigma^2_{blank}$ | 129 | |
| $\sigma^2/2 \cdot \mu^2$ | 0.067 | |
| $\mu/\sigma^2$ | 7.69 | 1/min |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 17/54.360, filed May 17, 2017 are incorporated by reference herein.

Example 1 (Optimally Adjusted Unit)

Consider a simulated moving bed unit constituted by 15 beds, each with a length of 1.24 m, with an interstitial porosity of 39.6%, and an internal radius of 1.05 m, with a feed injection, a desorbant injection, an extract withdrawal and a raffinate withdrawal.

The adsorbent under consideration was a type BaX zeolitic solid characterized by means of breakthrough using the above described method by a ratio $\mu/\sigma^2=7.69$ l/min.

The desorbant was paradiethylbenzene. The temperature was 175° C.; the pressure was 15 bar. The water content was 95 ppm (by weight).

The feed to be separated was composed of 50% of paraxylene, 17.3% of orthoxylene, 22.7% of metaxylene and 10% of ethylbenzene.

The shifts for the various injection or withdrawal points were simultaneous. The beds were distributed into 4 chromatographic zones in accordance with the configuration 3/5/5/2.

The flow rates for injecting the feed and desorbant were as follows:

0.393 m$^3$·min$^{-1}$ for the feed,
0.591 m$^3$·min$^{-1}$ for the desorbant.

In addition, the flow rate for zone 4 was 1.527 m$^3$·min$^{-1}$, and the extract withdrawal flow rate was 0.377 m$^3$·min$^{-1}$. The weighted cycle time was 396.1 m$^{-1}$.

By simulation, a paraxylene purity of 99.78% was obtained with a paraxylene yield of 97.7% with a productivity of 146.0 kg$_{PX}$·h$^{-1}$·m$^{-3}$.

This level of performance in terms of purity and yield of paraxylene was in compliance with the targets for the process and were taken as a reference for the subsequent examples.

Example 2 ("Underperforming" Unit)

Starting from the unit being considered to be optimally adjusted in terms of purity and yield of paraxylene as presented in Example 1, the cycle time was to be reduced in order to improve productivity, retaining the same desorbant ratio.

Again, a simulated moving bed unit was considered which was constituted by 15 beds, with a length of 1.24 m, an interstitial porosity of 39.6%, and an internal radius of 1.05 m, with a feed injection, a desorbant injection, an extract withdrawal and a raffinate withdrawal.

The adsorbent under consideration was a type BaX zeolitic solid characterized by means of breakthrough using the above described method by a ratio $\mu/\sigma^2=7.69$ l/min.

The desorbant was paradiethylbenzene. The temperature was 175° C.; the pressure bar.

The water content was 95 ppm (by weight).

The feed to be separated was composed of 50% of paraxylene, 17.3% of orthoxylene, 22.7% of metaxylene and 10% of ethylbenzene.

The shifts for the various injection or withdrawal points were simultaneous. The beds were distributed into 4 chromatographic zones in accordance with the configuration 3/5/5/2.

The flow rates for injecting the feed and desorbant were as follows:

0.431 m$^3$·min$^{-1}$ for the feed,
0.648 m$^3$·min$^{-1}$ for the desorbant.

In addition, the flow rate for zone 4 was 1.676 m$^3$·min$^{-1}$, and the extract withdrawal flow rate was 0.414 m$^3$·min$^{-1}$. The weighted cycle time was 360.8 m$^{-1}$.

By simulation, a paraxylene purity of 99.69% was obtained with a paraxylene yield of 97.3% with a productivity of 159.6 kg$_{PX}$·h$^{-1}$·m$^{-3}$. The unit adjusted in this manner was thus an "underperforming" unit compared with the purity and yield targets which were respectively 99.78% and 97.7%.

Example 3 ("Overperforming" Unit)

Starting from the unit considered in Example 1, the cycle time was to be increased in order to improve performances in terms of purity and paraxylene yield, retaining the same desorbant ratio.

Again, a simulated moving bed unit was considered which was constituted by 15 beds, with a length of 1.24 m, an interstitial porosity of 39.6%, and an internal radius of 1.05 m, with a feed injection, a desorbant injection, an extract withdrawal and a raffinate withdrawal.

The adsorbent under consideration was a type BaX zeolitic solid characterized by means of breakthrough using the above described method by a ratio $\mu/\sigma^2=7.69$ l/min.

The desorbent was paradiethylbenzene. The temperature was 175° C.; the pressure was 15 bar. The water content was 95 ppm (by weight).

The feed to be separated was composed of 50% of paraxylene, 17.3% of orthoxylene, 22.7% of metaxylene and 10% of ethylbenzene.

The shifts for the various injection or withdrawal points were simultaneous. The beds were distributed into 4 chromatographic zones in accordance with the configuration 3/5/5/2.

The flow rates for injecting the feed and desorbant were as follows:

0.361 m³·min⁻¹ for the feed,
0.542 m³·min⁻¹ for the desorbant.

In addition, the flow rate for zone 4 was 1.402 m³·min⁻¹, and the extract withdrawal flow rate was 0.346 m³·min⁻¹. The weighted cycle time was 431.4 m⁻¹.

By simulation, a paraxylene purity of 99.84% was obtained with a paraxylene yield of 97.9% with a productivity of 134.4 $kg_{PX} \cdot h^{-1} \cdot m^{-3}$. The unit adjusted in this manner was thus overperforming compared with the purity and yield targets which were respectively 99.78% and 97.7%.

These examples clearly illustrate the importance of adjusting the process in accordance with the invention in order to determine the cycle time which can be used to obtain optimized performances for a given desorbant ratio, namely simultaneously the target levels for purity and paraxylene yield as well as the maximum productivity for these adjustments.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for separating xylenes of a feed (F) to be fractionated in a simulated moving bed with a view to optimizing the purity and yield of paraxylene, the weight content of paraxylene in the feed (F) being in the range 25.01% to 60% by weight, the unit implementing said process using a number of beds in the range 4 to 24 and more preferably in the range 8 to 15, and the distribution of the beds in the various zones being given by the following general formula, which is valid irrespective of the total number of beds (N_total), the index z denoting the number of beds in the zone under consideration, and the second index being that of the zone under consideration:

$Nz1=(N\_total*5/24)*(1\pm0.2)$ $Nz2=(N\_total*9/24)*(1\pm0.2)$ $Nz3=(N\_total*7/24)*(1\pm0.2)$ $Nz4=(N\_total*3/24)*(1\pm0.2)$ the 4 chromatographic zones being defined as follows:

Zone 1: paraxylene desorption zone, included between the injection of the desorbant (D) and the withdrawal of the extract (E);

Zone 2: zone for the desorption of isomers of paraxylene, included between the withdrawal of the extract (E) and the injection of the feed (F) to be fractionated;

Zone 3: paraxylene adsorption zone, included between the injection of the feed and the withdrawal of the raffinate (R);

Zone 4: zone located between the withdrawal of the raffinate (R) and the injection of the desorbant (D), the optimized cycle time (interval of time separating two injections of desorbant to the same location in the column) being determined from the cycle time weighted by means of a correcting factor:

$$\frac{\mu}{\sigma^2} \cdot \frac{1}{\varepsilon_i \cdot L_{lit}}$$

the parameter $$\frac{\mu}{\sigma^2}$$

being itself determined by a breakthrough experiment, knowing the length of a bed ($L_{lit}$) and its interstitial porosity ($\varepsilon_i$), the measurement of $\sigma^2$ obtained in the presence of adsorbent having to be at least 10 times higher, preferably 30 times higher than the measurement $\sigma^2_{blank}$ obtained during a test carried out in the absence of adsorbent, with glass beads with a diameter approximately equal to that of the particles of adsorbent, the ratio of the flow rate of desorbant to the flow rate of paraxylene (QD/QPX), and thus the optimized desorbant flow rate, being determined by means of the following 3 tables as a function of the content of paraxylene in the feed:

TABLE 1

Paraxylene PX in the feed: $25\% < \%_{PX, feed} \leq 30\%$
25% < Paraxylene PX in the feed ≤ 30%

|  | t_cycle wtd (1/m) | $Q_D/Q_{PX}$ |
| --- | --- | --- |
| Adjustment No 1 | 320 +/− 25 | 5.30 +/− 0.55 |
| Adjustment No 2 | 345 +/− 25 | 4.85 +/− 0.50 |
| Adjustment No 3 | 370 +/− 25 | 4.50 +/− 0.45 |
| Adjustment No 4 | 395 +/− 25 | 4.20 +/− 0.45 |
| Adjustment No 5 | 425 +/− 25 | 4.00 +/− 0.45 |
| Adjustment No 6 | 465 +/− 25 | 3.75 +/− 0.40 |
| Adjustment No 7 | 510 +/− 25 | 3.60 +/− 0.40 |
| Adjustment No 8 | 560 +/− 30 | 3.55 +/− 0.40 |

TABLE 2

Paraxylene PX in the feed: $30\% < \%_{PX, feed} \leq 45\%$
30% < Paraxylene PX in the feed ≤ 45%

|  | t_cycle wtd (1/m) | $Q_D/Q_{PX}$ |
| --- | --- | --- |
| Adjustment No 1 | 325 +/− 25 | 4.40 +/− 0.45 |
| Adjustment No 2 | 345 +/− 25 | 4.00 +/− 0.40 |
| Adjustment No 3 | 365 +/− 25 | 3.75 +/− 0.40 |
| Adjustment No 4 | 385 +/− 25 | 3.50 +/− 0.40 |
| Adjustment No 5 | 415 +/− 25 | 3.30 +/− 0.35 |
| Adjustment No 6 | 445 +/− 25 | 3.15 +/− 0.35 |
| Adjustment No 7 | 485 +/− 25 | 3.00 +/− 0.35 |
| Adjustment No 8 | 530 +/− 25 | 2.90 +/− 0.35 |

TABLE 2-continued

Paraxylene PX in the feed: 30% < %$_{PX, feed}$ ≤ 45%
30% < Paraxylene PX in the feed ≤ 45%

| | t_cycle wtd (1/m) | $Q_D/Q_{PX}$ |
|---|---|---|
| Adjustment No 9 | 580 +/− 30 | 2.80 +/− 0.30 |
| Adjustment No 10 | 640 +/− 30 | 2.80 +/− 0.30 |

TABLE 3

Paraxylene PX in the feed: 45% < %$_{PX, feed}$ ≤ 60%
45% < Paraxylene PX in the feed ≤ 60%

| | t_cycle wtd (1/m) | $Q_D/Q_{PX}$ |
|---|---|---|
| Adjustment No 1 | 315 +/− 25 | 4.10 +/− 0.50 |
| Adjustment No 2 | 335 +/− 25 | 3.65 +/− 0.45 |
| Adjustment No 3 | 350 +/− 25 | 3.25 +/− 0.35 |
| Adjustment No 4 | 370 +/− 25 | 3.05 +/− 0.35 |
| Adjustment No 5 | 400 +/− 25 | 2.80 +/− 0.35 |
| Adjustment No 6 | 440 +/− 25 | 2.65 +/− 0.30 |
| Adjustment No 7 | 480 +/− 25 | 2.55 +/− 0.30 |

TABLE 3-continued

Paraxylene PX in the feed: 45% < %$_{PX, feed}$ ≤ 60%
45% < Paraxylene PX in the feed ≤ 60%

| | t_cycle wtd (1/m) | $Q_D/Q_{PX}$ |
|---|---|---|
| Adjustment No 8 | 525 +/− 25 | 2.45 +/− 0.30 |
| Adjustment No 9 | 580 +/− 30 | 2.40 +/− 0.30 |
| Adjustment No 10 | 640 +/− 30 | 2.35 +/− 0.30. |

2. The simulated moving bed xylenes separation process as claimed in claim 1, in which the operating temperature is in the range 100° C. and 250° C., and the pressure is between the bubble pressure of the mixture of xylenes constituting the feed and 3 MPa.

3. The simulated moving bed xylenes separation process as claimed in claim 1, in which the water content in the feed is in the range 70 to 140 ppm.

4. The simulated moving bed xylenes separation process as claimed in claim 1, in which the desorbant is paradiethylbenzene.

\* \* \* \* \*